(12) United States Patent
Schluess et al.

(10) Patent No.: US 6,241,661 B1
(45) Date of Patent: Jun. 5, 2001

(54) SELECTING LIMIT VALUES IN PARTICULAR FOR PATIENT MONITORING SYSTEMS

(75) Inventors: Rainer Schluess; Nikolai Marinow, both of Bondorf; Philipp Heusel, Hildrizhausen, all of (DE)

(73) Assignee: Hewlett-Packard Company, Palo Alto, CA (US)

( * ) Notice: Subject to any disclaimer, the term of this patent is extended or adjusted under 35 U.S.C. 154(b) by 0 days.

(21) Appl. No.: 09/368,816

(22) Filed: Aug. 5, 1999

(30) Foreign Application Priority Data

Aug. 7, 1998 (EP) .................................................. 98114861

(51) Int. Cl.⁷ ........................................................ A61B 5/00
(52) U.S. Cl. ................................................................ 600/300
(58) Field of Search ..................................... 600/300, 301, 600/481, 508, 528, 529; 128/897

(56) References Cited

U.S. PATENT DOCUMENTS

| | | | |
|---|---|---|---|
| 4,197,854 | * | 4/1980 | Kasa ........................................ 600/301 |
| 4,403,215 | * | 9/1983 | Hofmann et al. ................... 340/573.1 |
| 4,994,790 | * | 2/1991 | Ishii et al. ........................... 340/573.1 |
| 5,226,416 | * | 7/1993 | Bethune et al. ...................... 600/310 |
| 5,331,549 | * | 7/1994 | Crawford, Jr. ....................... 600/513 |
| 5,438,983 | * | 8/1995 | Falcone ................................ 600/301 |
| 5,464,012 | * | 11/1995 | Falcone ................................ 600/301 |
| 5,584,291 | * | 12/1996 | Vapola et al. ........................ 600/301 |
| 5,794,625 | * | 8/1998 | McCarley et al. ................... 600/549 |
| 5,860,918 | * | 1/1999 | Schradi et al. ....................... 600/300 |

FOREIGN PATENT DOCUMENTS

| | | |
|---|---|---|
| 1548059 | 11/1968 | (FR) . |
| 2281781A | 9/1994 | (GB) . |
| WO89/12420 | 1/1999 | (WO) . |

* cited by examiner

*Primary Examiner*—Cary O'Connor
*Assistant Examiner*—Navin Natnithithadha

(57) ABSTRACT

Disclosed is the selecting of a limit value, such as an alarm limit, from a range of limit values dependent on a starting value. The selected limit value is applicable e.g. in a patient monitoring system for monitoring a physiological parameter for providing a signal when a monitored value of the physiological parameter exceeds the selected limit value. According to the invention, the range of limit values comprises a functional range with a functional relationship of the limit values to the starting values, and at least one non-functional range with no functional relationship of the limit values to the starting values.

7 Claims, 1 Drawing Sheet

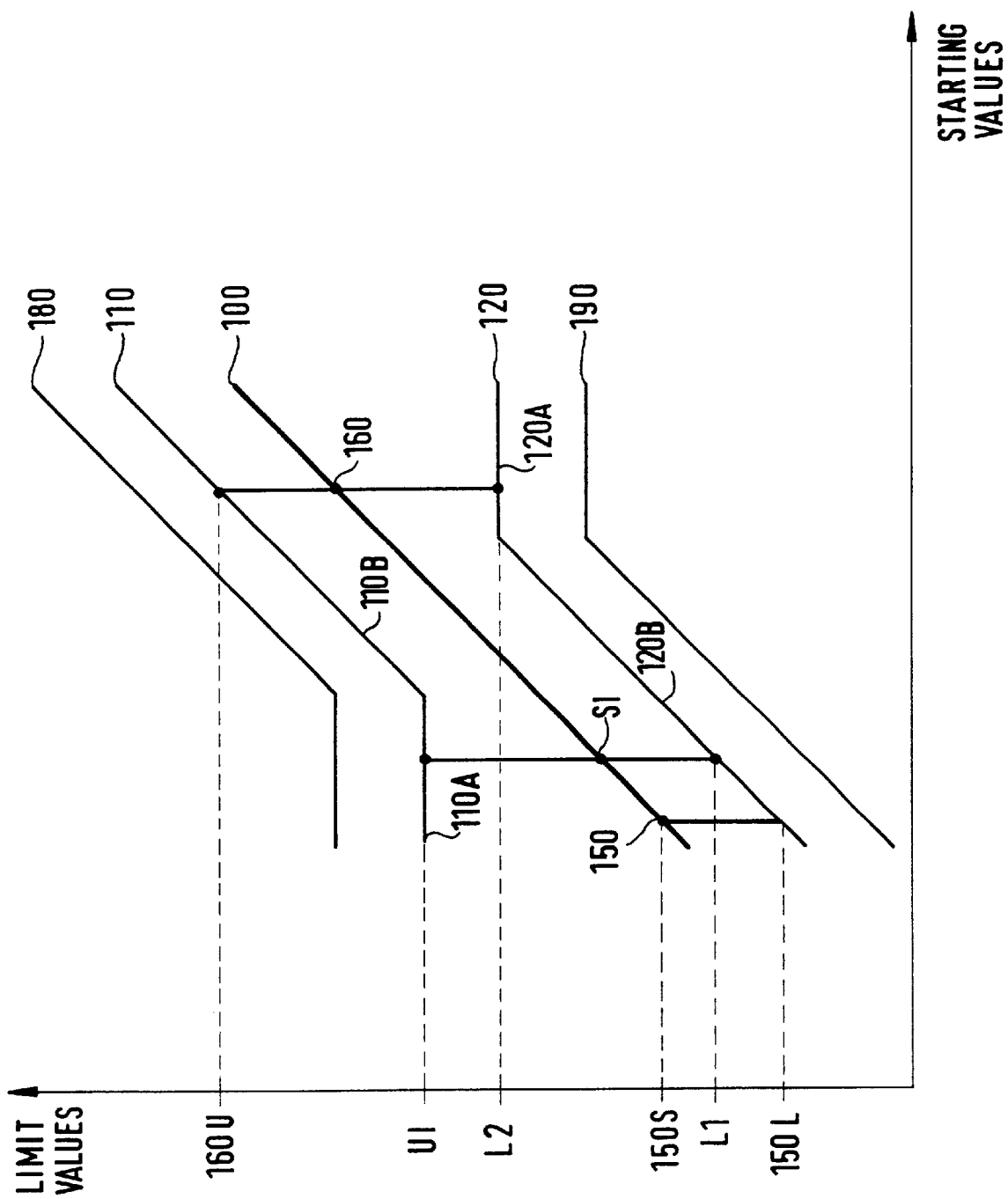

SELECTING LIMIT VALUES IN PARTICULAR FOR PATIENT MONITORING SYSTEMS

BACKGROUND OF THE INVENTION

The present invention relates to the selection of a limit value, such as an alarm limit, from a range of limit values, in particular for patient monitoring systems.

In today's patient monitoring systems, one of the most important tasks is to monitor the condition and/or status of a patient and to alarm medical staff in case that one or more monitored physiological parameters of the patient exceed a predefined upper or lower alarm limit. These alarm limits may either be set manually, e.g. by the medical staff, or can be set automatically, e.g. at a start of a measurement or on a user request. The alarm limit may be set as a fixed limit for each physiological parameter or can be based upon one or more current values of the physiological parameter of the patient e.g. determined by the patient monitoring system.

U.S. Pat. No. 4,994,790 discloses a method for setting an alarm in an apparatus for monitoring a plurality of patients. A present time value, an upper and a lower limit of a living body signal of one of the patients is indicated. A limit or threshold value of the upper limit and the lower limit can be set based upon the present time value of the living body signal by depressing an appropriate key of a keyboard.

U.S. Pat. No. 5,226,416 discloses an apparatus for monitoring output signals from a sensor. Upper and lower alarm levels are defined based on initial value or values determined by the sensor.

In case that the alarm limits are set automatically by the monitoring device, there are several ways to calculate the alarm limit based upon the patient's signals. In U.S. Pat. No. 5,226,416 and U.S. Pat. No. 4,994,790, a linear formula is used to calculate the upper and lower alarm limits. In general, simple formulas are used to calculate the alarm limits either by adding/subtracting a parameter specific offset to/from a current value, by multiplying the current value with a parameter specific factor, or by a combination of both. However, all of the known algorithms to calculate the alarm limits exhibit the disadvantage that they are not flexible enough and might lead to an unnecessary alarming of the monitoring system.

SUMMARY OF THE INVENTION

It is an object of the present invention to provide more flexible alarm limits for monitoring physiological parameters of a patient. The object is solved by the independent claims. Preferred embodiments are shown by the dependent claims.

According to the invention, an alarm limit (or threshold value) applied e.g. for monitoring a physiological parameter comprises at least one range with a functional relationship of the values of the physiological parameter and at least one range with no functional relationship to the values of the physiological parameter. This allows to adapt alarm limits to ranges of 'normal' conditions of the physiological parameter, so that an unnecessary alarming of the monitoring device can be avoided, e.g. in case that a patient status recovers and returns to "normal" values.

BRIEF DESCRIPTION OF THE DRAWINGS

Other objects and many of the attendant advantages of the present invention will be readily appreciated and become better understood by reference to the following detailed description when considering in connection with the accompanied drawing, wherein:

FIG. 1 shows a preferred embodiment according to the invention depicting different ranges for the alarm limits.

DETAILED DESCRIPTION OF THE INVENTION

FIG. 1 shows a preferred embodiment according to the invention depicting different ranges for the alarm limits. A range of physiological meaningful values is depicted as line 100. Line 110 shows a range of upper limits indicating that an alarm will be triggered when a value of a measured physiological parameter is greater than the respective limit. Accordingly, a line 120 depicts a range of lower limits indicating that an alarm will be triggered when the value of the physiological parameter is smaller than the respective limit.

The values of line 100 represent starting values S1 for (e.g. automatically) assigning alarm limits based on each starting value. In an example, when alarm limits have to be assigned based on a starting value S1 of a parameter, the upper limit will be set to a value U1 by a projection of S1 in the direction of the y-axis on line 110. Accordingly, the lower limit will be set to a value L1 by a projection of S1 in the direction of the y-axis on line 120. The values U2 and of the limits can be derived from FIG. 1 by a projection on the y-axis.

The upper limit 110 comprises a first range 110A, wherein the value of the upper limit is no mathematical function of the values of the physiological parameter, and a second range 110B, wherein the values of the upper limit can be represented by a mathematical function of the values of the physiological parameter. In the example of FIG. 1, the upper limit in the range 110A is represented by a constant value U1 and the values in the range 110B are defined by a pre-given relative (e.g. +x %) or absolute (e.g. +x) relation to the values S of the physical parameter.

Accordingly, the lower limit 120 comprises a first range 120A, wherein the values of the lower limit do not represent a function of the values of the physiological parameter, and a second range 120B, wherein the values of the lower limit represent a function of the values of the physiological parameter. In the example of FIG. 1, the values in the range 120A represent a constant value L2, whereas the values of the lower limit 120 in the range 120B are determined by a relative or absolute function of the values of the physiological parameter.

In the example of FIG. 1, the upper limit 110 and the lower limit 120 are selected in a way that unnecessary alarms can be avoided. E.g. for low values of the physiological parameter, an alarm is only triggered when the patient's condition gets worse (i. e. when the values of the physiological parameter go in the direction of the lower limit 120). When the patient's condition recovers (i. e. when the values of the physiological parameter go in the direction of the upper limit 110), an alarm will be first triggered when the upper limit 110 is reached (i.e. for values greater or equal to U1).

In the specific example of FIG. 1, alarm limits lying in a range between range 110A (U1) and range 120A (L2) will not be set for any one of the starting values S. Preferably, this no-alarm range (between U1 and L1) is selected to contain the normal uncritical values of the physiological parameter. The value (U1) of the upper (no-alarm) range 110A is preferably selected as an upper patient vital sign value that is uncritical for any 'normal' patient, whereas the value (L2)

of the lower (no-alarm) range 120A is preferably selected as the lowest vital sign value that is non-critical for 'normal' patients. Thus, unnecessary alarms are avoided when the values of the physiological parameter only represent physiologically uncritical, normal values.

The invention shall now be explained for an example, wherein the physiological parameter represents a patient's heart rate. However, it is clear that the principles of the invention apply to any physiological parameter. When the patient has a low heart rate, so that the starting value to define the alarm limits is e.g. at a point 150, the lower limit 120 has to be set narrow to the starting value in order to alert the medical staff if the patient's condition gets even worse. A value 150L of the lower limit 120 is determined dependent on the starting value 150S. However, if the patient recovers and the heart rate lies within normal uncritical values lower than the upper limit U1, as defined by range 110A, no alarm will be generated. Accordingly, when the patient has a high heart rate, e.g. with a starting value at a point 160, the monitoring device adjusts the upper limit 110 according to a parameter specific formula to a value 160U, whereas the lower limit 120 in the range 120A is set below the normal uncritical values of the heart rate to the value L2, as defined by the range 120A. When the patient recovers from the high heart rate to a lower heart rate, no alarm will be generated until the heart rate goes below the lower limit L2.

In a preferred embodiment, the distance of an alarm limit to the starting values S of line 100 can be varied by the user. The user can determine the distance between the alarm limits and the starting values, may have a choice between a set of predefined distances of the alarm limits to the starting values S, or a combination of both. In the example of FIG. 1, the user has a choice for selecting the upper limit between a narrow limit, defined by line 110, and a wide limit defined by a line 180. The lower limit can be selected as a narrow limit, defined by line 120, or a wide limit defined by a line 190. The user can either select wide or narrow limits for the upper and the lower limits, or, in a further embodiment, for each limit separately. A variation of the distances of the alarm limits is in particular useful e.g. during a monitoring in an operating room, where it is sometimes necessary to set the alarm limit(s) depending on the phase of an operation/surgery or, in general, depending on the patient's situation. Preferably, the alarm limits are set 'narrow' if the patient is a critical patient, otherwise 'wide' for 'normal' patients. A variation of the distances is preferably accomplished by providing specific keys in the patient monitoring system.

In another embodiment, it is prevented to (manually) change the distances of the alarm limits, if the starting values exceed critical values of the physiological parameter, in order not to put a risk on the patient.

For indicating a change of alarm limits, changed alarm limits are preferably highlighted, displayed inverse, or otherwise indicated on a monitoring screen e.g. for a preconfigured period of time. In one embodiment, the patient monitoring system provides a special configuration mode, wherein the user can disable the functionality for an automatic setting of the alarm limits based on the starting values. This is especially useful if the alarm limits for a specific parameter (e.g. $SaO_2$) are set to identical values for the whole unit in a hospital and the limits should not be changed with auto-limits. The disabling can be selected for individual parameters or for all parameters.

The definition of the alarm limits according to the invention can be based on criteria such as the type of the physiological parameter (e.g. heartrate, respiration rate, invasive blood pressure, temperature, oxygen saturation $SaO_2$, $CO_2$, ST, non-invasive blood pressure, the patient size (e.g. adult, pediatric, neonate) and/or a label (e.g. arterial blood pressure ABP, pulmonary arterial blood pressure PAP, inter-cranial pressure ICP, or central venous pressure CVP), so that the shape of the alarm limit(s) can be adapted to the corresponding parameter(s).

The shape of the alarm limit(s) is preferably based on average patient data, such as typical uncritical/critical conditions for ranges of lower and/or higher starting values.

The starting value for selecting the alarm limits can be determined by any means as known in the art, such as by averaging a number of measuring values, selecting the present time-value, an initial value, a 'median' value, or any other appropriately (e.g. digitally) filtered parameter value. In a preferred embodiment, an averaging period (e.g. 12 s) exemplifies a compromise between short response times and a smooth value that represents the current patient's status. Depending on the parameter, either a 12-second median value is taken or an average value of the last 12 seconds is used for automatic limit calculations. In case of non-continuous measurements like non-invasive blood pressure, the last (valid) measurement(s) is/are used. alarm limits are preferably only adjusted in an uncritical physiological range, where no additional risk is put on the patient, and/or in a way that the monitoring system will not generate an alarm if the patient's situation recovers after setting the alarm limits. Ranges (e.g. ranges 110A or 120A) with alarm limits calculated with a functional relationship to the starting value are preferably only provided within a range of values that usually does not put any risk on the patient. In one embodiment, when the user wants to change the alarm limits for values of the physiological parameter in a patient critical range, the user has to do that manually by means of specific procedures and no automatic setting of the alarm limits takes place dependent on the respective starting.

In one embodiment, the range of upper limits 110 of FIG. 1 further comprises a non-functional range for higher values of the starting values. Accordingly, the range of lower limits 120 of FIG. 1 might further comprise a non-functional range for lower values of the starting values. This ensures that possible risks for the patient due to excessive upper or lower limits can be reduced or avoided.

What is claimed is:

1. An apparatus for selecting a limit value from a range of limit values dependent on a starting value, whereby the selected limit value is applicable in a system for monitoring a physiological parameter for providing a signal when a monitored value of the physiological parameter exceeds the selected limit value, wherein, for at least one first range of starting values a value of the limit remains substantially constant over the first range of starting values, and for a second range of starting values the value of the limit varies as a function of the value of the starting value over the second range of starting values.

2. The apparatus of claim 1, wherein for said first range of starting values a value of a lowest upper limit in a range of upper limits remains substantially constant over the first range of starting values, and for said second range of starting values a value of a highest lower limit in a range of lower limits remains substantially constant over the second range of starting values.

3. The apparatus of claim 2, wherein the lowest upper limit value and the highest lower limit value define a range of uncritical values.

4. The apparatus according to claim 1, further comprising means for varying the distance of the range of limit values from a range of starting values.

5. A patient monitoring system for monitoring a physiological parameter of a patient, comprising the apparatus according to claim 1, whereby the selected limit value is used for providing a signal when a monitored value of the physiological parameter exceeds the selected limit value.

6. A method for selecting a limit value, whereby the selected limit value is applied in a system for monitoring a physiological parameter for providing a signal when a monitored value of the physiological parameter exceeds the selected limit value, the method comprising the steps of:

provdiing a range of limit values wherein, for at least one first range of starting values a value of the limit remains substantially constant over the first range of starting values, and for a second range of starting values the value of the limit varies as a function of the value of the starting value over the second range of starting values, and selecting the limit value from the range of limit values dependent on a starting value.

7. An apparatus for selecting a limit value from a range of limit values dependent on a starting value, whereby the selected limit value is applicable in a system for monitoring a physiological parameter for providing a signal when a monitored value of the physiological parameter exceeds the selected limit value, wherein, for at least one first range of starting values a value of at least one of an upper limit or a lower limit remains substantially constant over the first range of starting values, and for a second range of starting values the values of both the upper limit and the lower limit vary as a function of the value of the starting value over the second range of starting values.

* * * * *